(12) United States Patent
Zuberi et al.

(10) Patent No.: US 8,946,448 B2
(45) Date of Patent: Feb. 3, 2015

(54) ORGANIC SEMICONDUCTORS (75) Inventors: Sheena Zuberi, Harrow (GB); Tania Zuberi, Harrow (GB)

(73) Assignee: Cambridge Display Technology Limited, Cambridgeshire (GB)

( * ) Notice: Subject to any disclaimer, the term of this patent is extended or adjusted under 35 U.S.C. 154(b) by 116 days.

(21) Appl. No.: 13/643,004

(22) PCT Filed: Apr. 20, 2011

(86) PCT No.: PCT/GB2011/000613
§ 371 (c)(1),
(2), (4) Date: Jan. 7, 2013

(87) PCT Pub. No.: WO2011/131936
PCT Pub. Date: Oct. 27, 2011

(65) Prior Publication Data
US 2013/0102792 A1 Apr. 25, 2013

(30) Foreign Application Priority Data
Apr. 23, 2010 (GB) .................. 1006832.8

(51) Int. Cl.
| C07D 333/18 | (2006.01) |
| H01L 51/00 | (2006.01) |
| C07D 495/06 | (2006.01) |
| C07D 495/22 | (2006.01) |
| C09B 69/10 | (2006.01) |
| C09B 3/78 | (2006.01) |
| H01L 27/32 | (2006.01) |
| H01L 51/05 | (2006.01) |

(52) U.S. Cl.
CPC .......... *H01L 51/0058* (2013.01); *C07D 333/18* (2013.01); *C07D 495/06* (2013.01); *C07D 495/22* (2013.01); *H01L 51/0036* (2013.01); *H01L 51/0056* (2013.01); *H01L 51/0094* (2013.01); *H01L 51/0071* (2013.01); *H01L 51/0074* (2013.01); *C09B 69/101* (2013.01); *C09B 69/102* (2013.01); *C09B 3/78* (2013.01); *H01L 27/3274* (2013.01); *H01L 51/0545* (2013.01)
USPC .......................................................... 549/4

(58) Field of Classification Search
CPC ..................................................... C07D 333/18
USPC ............................................................ 549/4
See application file for complete search history.

(56) References Cited

FOREIGN PATENT DOCUMENTS

| JP | 10-340785 A | 12/1998 |
| JP | 2007-027356 A | 2/2007 |
| JP | 2007-088222 A | 4/2007 |
| JP | 2008-288247 A | 11/2008 |
| JP | 2010-034460 A | 2/2010 |
| WO | WO-00/53656 A1 | 9/2000 |
| WO | WO-2007/068618 A1 | 6/2007 |
| WO | WO-2007/116660 A1 | 10/2007 |
| WO | WO-2009/130991 A1 | 10/2009 |

OTHER PUBLICATIONS

King, Med. Chem., Principle and Practice (1994), pp. 206-208.*
Bünnagel et al., "Thiophene-Phenylene/Naphthalene-Based Step-Ladder Copolymers," *J. Poly. Sci. A: Poly. Chem.*, 46(22):7342-4353 (2008).
Smet et al., "A General Synthesis of Disubstituted Rubicenes," *Eur. J. Org. Chem.*, 12:2769-2773 (1998).
Smet et al., "An Improved Synthesis of Substituted Rubicenes Providing Access to Heterocyclic Rubicene Analogues," *Synlett.*, 4:495-497 (1999).
Yamamoto, "Electrically Conducting and Thermally Stable π-Conjugated Poly(Arylene)s Prepared by Organometallic Processes," *Prog. Polym. Sci.*, 17:1153-1205 (1993).
International Preliminary Report on Patentability for Application No. PCT/GB2011/000613, dated Oct. 23, 2012.
International Search Report and Written Opinion for Application No. PCT/GB2011/000613, dated Aug. 5, 2011.
Search Report for Application No. GB1006832.8, dated Aug. 17, 2010.

* cited by examiner

*Primary Examiner* — Taofiq A Solola
(74) *Attorney, Agent, or Firm* — Marshall, Gerstein & Borun LLP (57) ABSTRACT

A semiconducting compound with the structure:

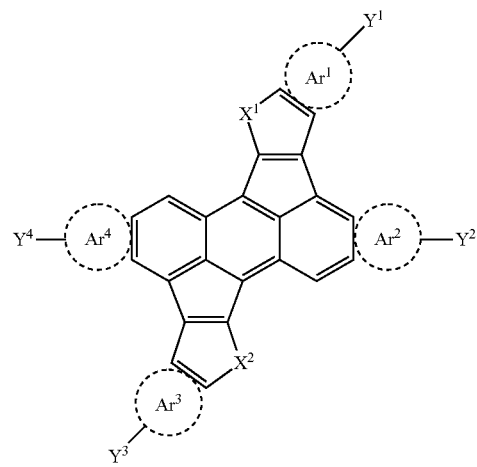

where $X^1$ and $X^2$ are independently S, Se, $SiR^1R^2$, O, $CR^3R^4$, $C_2R^5R^6$, N, $NR^7$, where $R^1$ to $R^7$ independently comprise hydrogen, straight, branched or cyclic alkyl, akenyl or alkynyl groups, alkoxy, aryl, silyl or amino; where each of $Ar^1$ to $Ar^4$ is optional and independently comprises, if present, an aryl or heteroaryl group; and where $Y^1$ to $Y^4$ independently comprise hydrogen, reactive groups, optionally substituted straight, branched or cyclic alkyl, alkoxy, akenyl, alkynyl, amido or amino groups, optionally substituted aryl or heteroaryl where at least one of $Y^1$ to $Y^4$ does not comprise hydrogen; and methods and devices related thereto.

12 Claims, 3 Drawing Sheets

ORGANIC SEMICONDUCTORS

BACKGROUND OF THE INVENTION

1. Field of the Invention

The present invention relates generally to organic semiconductors and in particular to organic semiconductors for forming part of a thin film transistor.

2. Related Technology

Transistors can be divided into two main types: bipolar junction transistors and field-effect transistors. Both types share a common structure comprising three electrodes with a semiconductive material disposed there between in a channel region. The three electrodes of a bipolar junction transistor are known as the emitter, collector and base, whereas in a field-effect transistor the three electrodes are known as the source, drain and gate. Bipolar junction transistors may be described as current-operated devices as the current between the emitter and collector is controlled by the current flowing between the base and emitter. In contrast, field-effect transistors may be described as voltage-operated devices as the current flowing between source and drain is controlled by the voltage between the gate and the source.

Transistors can also be classified as p-type and n-type according to whether they comprise semiconductive material which conducts positive charge carriers (holes) or negative charge carriers (electrons) respectively. The semiconductive material may be selected according to its ability to accept, conduct, and donate charge. The ability of the semiconductive material to accept, conduct and donate holes or electrons can be enhanced by doping the material.

For example, a p-type transistor device can be formed by selecting a semiconductive material which is efficient at accepting, conducting, and donating holes, and selecting a material for the source and drain electrodes which is efficient at injecting and accepting holes from the semiconductive material. Good energy-level matching of the Fermi-level in the electrodes with the HOMO level of the semiconductive material can enhance hole injection and acceptance. In contrast, an n-type transistor device can be formed by selecting a semiconductive material which is efficient at accepting, conducting, and donating electrons, and selecting a material for the source and drain electrodes which is efficient at injecting electrons into, and accepting electrons from, the semiconductive material. Good energy-level matching of the Fermi-level in the electrodes with the LUMO level of the semiconductive material can enhance electron injection and acceptance.

Transistors can be formed by depositing the components in thin films to form a thin film transistor (TFT). When an organic material is used as the semiconductive material in such a device, it is known as an organic thin film transistor (OTFT).

OTFTs may be manufactured by low cost, low temperature methods such as solution processing. Moreover, OTFTs are compatible with flexible plastic substrates, offering the prospect of large-scale manufacture of OTFTs on flexible substrates in a roll-to-roll process.

Figure 2:
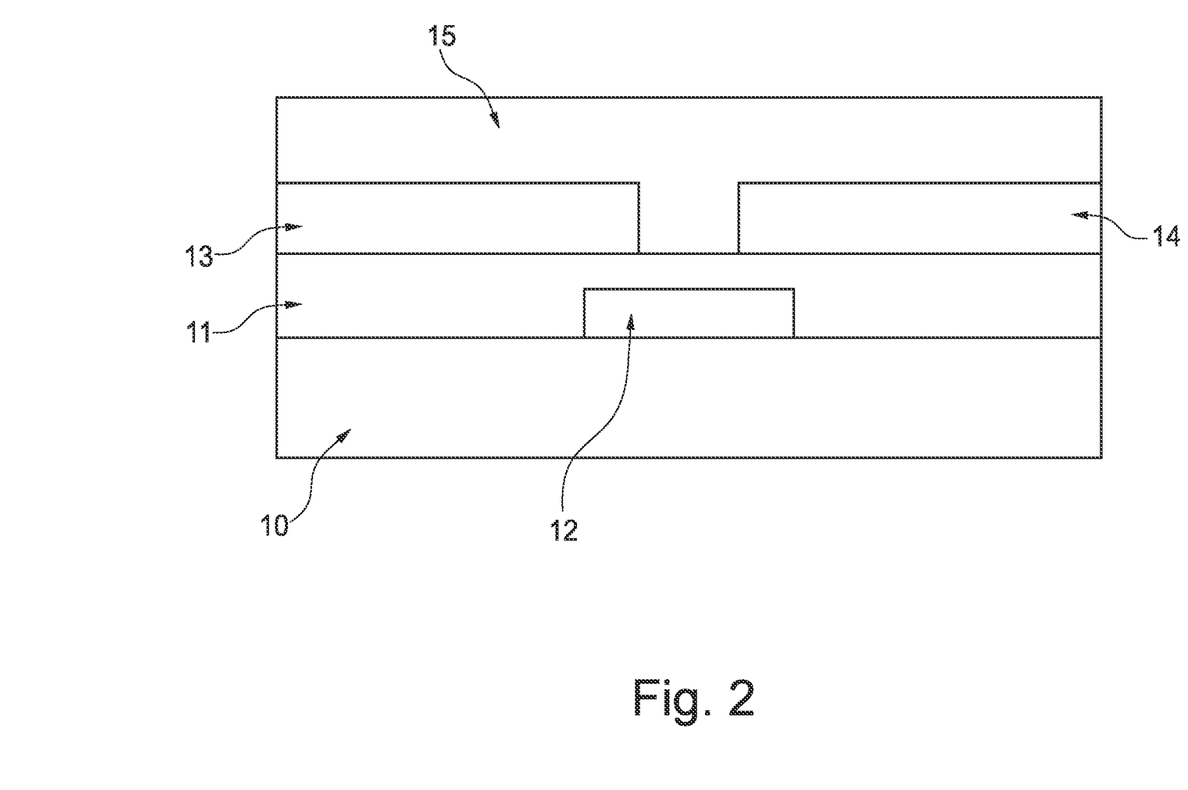
FIG. 2 is a schematic diagram of a general architecture of a bottom-gate organic thin film transistor according to the prior art.

With reference to FIG. 2, the general architecture of a bottom-gate organic thin film transistor (OTFT) comprises a gate electrode 12 deposited on a substrate 10. An insulating layer 11 of dielectric material is deposited over the gate electrode 12 and source and drain electrodes 13, 14 are deposited over the insulating layer 11 of dielectric material. The source and drain electrodes 13, 14 are spaced apart to define a channel region therebetween located over the gate electrode 12. An organic semiconductor (OSC) material 15 is deposited in the channel region for connecting the source and drain electrodes 13, 14. The OSC material 15 may extend at least partially over the source and drain electrodes 13, 14.

Alternatively, it is known to provide a gate electrode at the top of an organic thin film transistor to form a so-called top-gate organic thin film transistor. In such an architecture, source and drain electrodes are deposited on a substrate and spaced apart to define a channel region there between. A layer of an organic semiconductor material is deposited in the channel region to connect the source and drain electrodes and may extend at least partially over the source and drain electrodes. An insulating layer of dielectric material is deposited over the organic semiconductor material and may also extend at least partially over the source and drain electrodes. A gate electrode is deposited over the insulating layer and located over the channel region.

An organic thin film transistor can be fabricated on a rigid or flexible substrate. Rigid substrates may be selected from glass or silicon and flexible substrates may comprise thin glass or plastics such as poly(ethylene-terephthalate) (PET), poly(ethylene-naphthalate) (PEN), polycarbonate and polyimide.

The organic semiconductive material may be solution processed through the use of a suitable solvent. Exemplary solvents include mono- or poly-alkylbenzenes such as toluene and xylene; tetralin; and chloroform. Preferred solution deposition techniques include spin coating and ink jet printing. Other solution deposition techniques include dip-coating, roll printing and screen printing.

The length of the channel defined between the source and drain electrodes may be up to 500 microns, but preferably the length is less than 200 microns, more preferably less than 100 microns, most preferably less than 20 microns.

The gate electrode can be selected from a wide range of conducting materials for example a metal (e.g. gold) or metal compound (e.g. indium tin oxide). Alternatively, conductive polymers may be deposited as the gate electrode. Such conductive polymers may be deposited from solution using, for example, spin coating or ink jet printing techniques and other solution deposition techniques discussed above.

The insulating layer comprises a dielectric material selected from insulating materials having a high resistivity. The dielectric constant, k, of the dielectric is typically around 2-3 although materials with a high value of k are desirable because the capacitance that is achievable for an OTFT is directly proportional to k, and the drain current ID is directly proportional to the capacitance. Thus, in order to achieve high drain currents with low operational voltages, OTFTs with thin dielectric layers in the channel region are preferred.

The dielectric material may be organic or inorganic. Preferred inorganic materials include $SiO_2$, $SiN_x$ and spin-on-glass (SOG). Preferred organic materials are generally polymers and include insulating polymers such as poly vinylalcohol (PVA), polyvinylpyrrolidine (PVP), acrylates such as polymethylmethacrylate (PMMA), fluorinated polymers and benzocyclobutanes (BCBs) available from Dow Corning. The insulating layer may be formed from a blend of materials or comprise a multi-layered structure.

The dielectric material may be deposited by thermal evaporation, vacuum processing or lamination techniques as are known in the art. Alternatively, the dielectric material may be deposited from solution using, for example, spin coating or ink jet printing techniques and other solution deposition techniques discussed above.

If the dielectric material is deposited from solution onto the organic semiconductor, it should not result in dissolution of the organic semiconductor. Likewise, the dielectric material should not be dissolved if the organic semiconductor is deposited onto it from solution. Techniques to avoid such dissolution include: use of orthogonal solvents for example use of a solvent for deposition of the uppermost layer that does not dissolve the underlying layer; and cross linking of the underlying layer.

The thickness of the insulating layer is preferably less than 2 micrometers, more preferably less than 500 nm.

Organic semiconductors are a class of organic molecules having extensively conjugated pi systems allowing for the movement of electrons.

Preferred methods for preparation of these molecules are Suzuki reactions (coupling or polymerization reactions) as described in, for example, WO 2000/53656 and Yamamoto polymerization as described in, for example, T. Yamamoto, "Electrically Conducting And Thermally Stable pi-Conjugated Poly(arylene)s Prepared by Organometallic Processes", Progress in Polymer Science 1993, 17, 1153-1205. These techniques both operate via a "metal insertion" wherein the metal atom of a metal complex catalyst is inserted between an aryl group and a leaving group of a monomer. In the case of Yamamoto polymerization, a nickel complex catalyst is used; in the case of Suzuki reaction, a palladium complex catalyst is used.

For example, in the synthesis of a linear polymer by Yamamoto polymerization, a monomer having two reactive halogen groups is used. Similarly, according to the method of Suzuki reaction, at least one reactive group is a boron derivative group such as a boronic acid or boronic ester and the other reactive group is a halogen. Preferred halogens are chlorine, bromine and iodine, most preferably bromine.

Alternatively, stannyl groups may be used as reactive groups in polymerization or coupling reactions (Stille reactions).

The performance of organic semiconductors is typically assessed by measurement of its "charge mobility" (cm$^2$ V$^{-1}$ s$^{-1}$), which may relate to either the mobility of holes or electrons. This measurement relates to the drift velocity of charge carriers to an applied electric field across a material.

Organic semiconductors having relatively high mobilities tend to be those which comprise compounds having a rigid planar structure with extensive conjugation which allows for efficient and effective pi-pi stacking in the solid state.

WO 2007/068618 describes a variety of organic semiconductors, each comprising an array of fused aromatic rings having a central benzene ring substituted with acetylene groups.

JP 2007/088222 and WO 2007/116660 describe the use of benzodithiophenes and its derivatives in small molecule, oligomeric and polymeric form, as organic semiconductors.

Scherf et al. in Journal of Polymer Science A: Polymer Chemistry 46(22) 7342 to 7353 describe polymers having the structure:

However, the increased level of conjugation required to allow compounds to form such a pi-pi stack may also result in a decrease in band gap and stability of the semiconductor, leading to poor performance and a short lifetime.

Moreover, these compounds may be highly insoluble due to the size of molecule required to achieve extended conjugation, which poses particular problems in synthesis and renders their use in efficient transistor production methods, such as ink-jet printing, difficult.

SUMMARY OF THE INVENTION

The present invention seeks to provide an organic semiconductor having high mobility, good solubility and good ambient stability.

In a first aspect, the invention provides a semiconducting compound comprising the structure:

where $X^1$ and $X^2$ are independently S, Se, SiR$^1$R$^2$, O, CR$^3$R$^4$, C$_2$R$^5$R$^6$, N, NR$^7$, where R$^1$ to R$^7$ independently comprise hydrogen, straight, branched or cyclic alkyl, akenyl or alkynyl groups, preferably having 1 to 20 carbons, alkoxy, aryl, silyl or amino;

where each of Ar$^1$ to Ar$^4$ is optional and independently comprises, if present, an aryl or heteroaryl group;

and where Y$^1$ to Y$^4$ independently comprise hydrogen, reactive groups, optionally substituted straight, branched or cyclic alkyl, alkoxy, akenyl, alkynyl, amido or amino groups, preferably having 1 to 20 carbon atoms, optionally substituted aryl or heteroaryl where at least one of Y$^1$ to Y$^4$ does not comprise hydrogen.

The inventors have surprisingly found that the two dimensional conjugated framework provided by the present invention affords excellent stability, enhances mobility and provides a low band gap when utilized as part of a semiconducting material.

Preferably, Ar$^1$ to Ar$^4$, if present, independently comprise heterocyclic groups having a heteroatom selected from the group: S, O, Si, N, Se.

Preferably, at least one, e.g. 2, 3 or all, of $Y^1$ to $Y^4$ comprises a solubilising group, e.g. a an optionally substituted straight, branched or cyclic alkyl, alkoxy, akenyl, alkynyl, amido or amino groups, preferably having 1 to 20 carbon atoms.

The inventors have surprisingly found that this preferable positioning of solubilising groups affords an excellent solubilising effect. Accordingly, shorter and/or smaller solubilising groups may be used at the preferred positions. These shorter and/or smaller solubilising groups are less able to interfere with ∏-∏ stacking, thereby potentially providing improved mobility in addition to improved solution processability.

Moreover, the improved solubility afforded by the positioning of the solubilising groups allows the planar conjugated structure of the semiconducting species to be further extended while the species remains soluble.

In some embodiments, the semiconducting compound comprises two or more, e.g. a pair of reactive or polymerisable groups, for example $Y^1$ and $Y^3$ or $Y^2$ and $Y^4$ may comprise reactive groups. The reactive polymer groups preferably independently comprise such moieties as halogens, boronic acids, diboronic acids, esters of boronic and diboronic acids, alkylene groups or stannyl groups.

In another aspect, the invention comprises a semiconducting oligomer or polymer having a structure:

where n is an integer between 2 and 10,000;
where $X^1$ and $X^2$ are independently S, Se, $SiR^1R^2$, O, $CR^3R^4$, $C_2R^5R^6$, N, $NR^7$, where $R^1$ to $R^7$ independently comprise hydrogen, straight, branched or cyclic alkyl, akenyl or alkynyl groups, preferably having 1 to 20 carbons, alkoxy, aryl, silyl or amino;

where each of $Ar^1$ to $Ar^4$ is optional and independently comprises, if present, an aryl or heteroaryl group;

and where $Y^1$ to $Y^4$ independently comprise hydrogen, reactive groups, optionally substituted straight, branched or cyclic alkyl, alkoxy, akenyl, alkynyl, amido or amino groups, preferably having 1 to 20 carbon atoms, optionally substantial aryl or heteroaryl where at least one of $Y^1$ to $Y^4$ does not comprise hydrogen.

The compound may be, for example, a monomer, oligomer, polymer or copolymer.

Preferably, n is an integer between 2 and 10, e.g. between 2 and 5.

Preferably the compound comprises a structure selected from the group:

-continued

-continued where F$_8$ comprises the structure:

In another aspect, the invention provides an electronic device comprising a semiconducting portion comprising a compound described herein.

In another aspect, the invention provides a solution for applying to the surface of a substrate to form a semiconducting portion on the substrate, the solution comprising a compound as described herein.

In a further aspect, the invention provides a method of manufacturing an electronic device comprising applying a solution as described herein onto a substrate.

BRIEF DESCRIPTION OF THE DRAWINGS

Embodiments of the invention will now be described with reference to the following drawings.

DETAILED DESCRIPTION

Throughout the following description like reference numerals shall be used to identify like parts.

Figure 1:
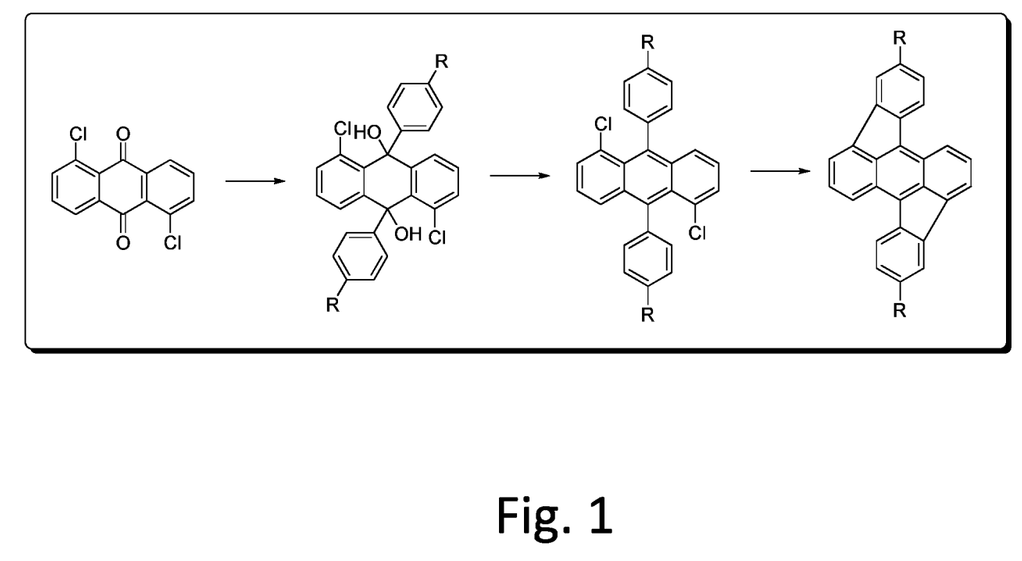
FIG. 1 shows a synthesis of a compound according to the invention.

Organic semiconductors according to the present invention may be manufactured by the synthesis shown as shown in FIG. 1.

The resulting compounds are easily soluble and may thus be applied by ink-jet printing onto a substrate to provide the semiconducting layer 15 in a thin film transistor such as is shown in FIG. 2 in order to provide an electronic device according to an aspect of the present invention.

An application of such an organic thin film transistor (OTFT) may be to drive pixels in an optical device, preferably an organic optical device. Examples of such optical devices include photoresponsive devices, in particular photodetectors, and light-emissive devices, in particular organic light emitting devices. OTFTs are particularly suited for use with active matrix organic light emitting devices, e.g. for use in display applications.

Figure 3:
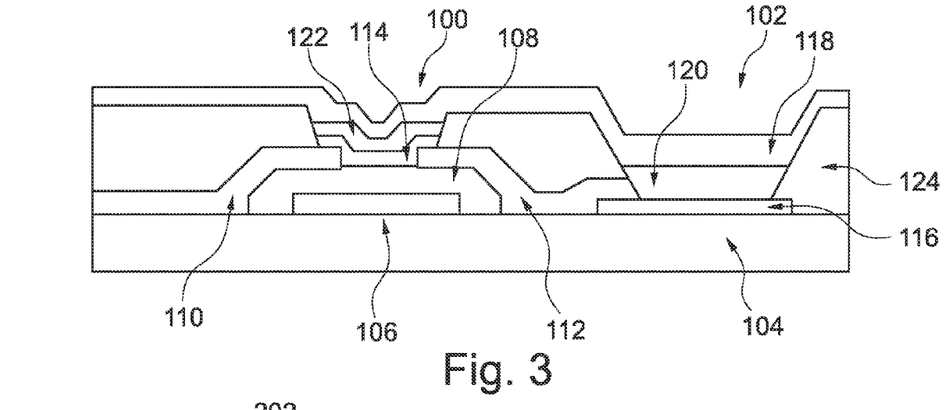
FIG. 3 is a schematic diagram of a pixel comprising an organic thin film transistor and an adjacent organic light emitting device fabricated on a common substrate according to an embodiment of the present invention; and, FIG. 4 is a schematic diagram of an organic thin film transistor fabricated in a stacked relationship to an organic light emitting device according to an embodiment of the present invention.

FIG. 3 shows a pixel comprising an organic thin film transistor 100 and an adjacent organic light emitting device (OLED) 102 fabricated on a common substrate 104. The OTFT 100 comprises gate electrode 106, dielectric layer 108, source and drain electrodes 110 and 112 respectively, and OSC layer 114. The OLED 102 comprises anode 116, cathode 118 and an electroluminescent layer 120 provided between the anode 116 and cathode 118. Further layers may be located between the anode 116 and cathode 118, such as charge transporting, charge injecting or charge blocking layers. In the embodiment of FIG. 3, the layer of cathode material 118 extends across both the OTFT 100 and the OLED 102, and an insulating layer 122 is provided to electrically isolate the cathode layer 118 from the OSC layer 122. The active areas of the OTFT 100 and the OLED 102 are defined by a common bank material formed by depositing a layer of photoresist 124 on substrate 104 and patterning it to define OTFT 100 and OLED 102 areas on the substrate.

In FIG. 3, the drain electrode 112 is directly connected to the anode 116 of the organic light emitting device 102 for switching the organic light emitting device 102 between emitting and non-emitting states.

Figure 4:
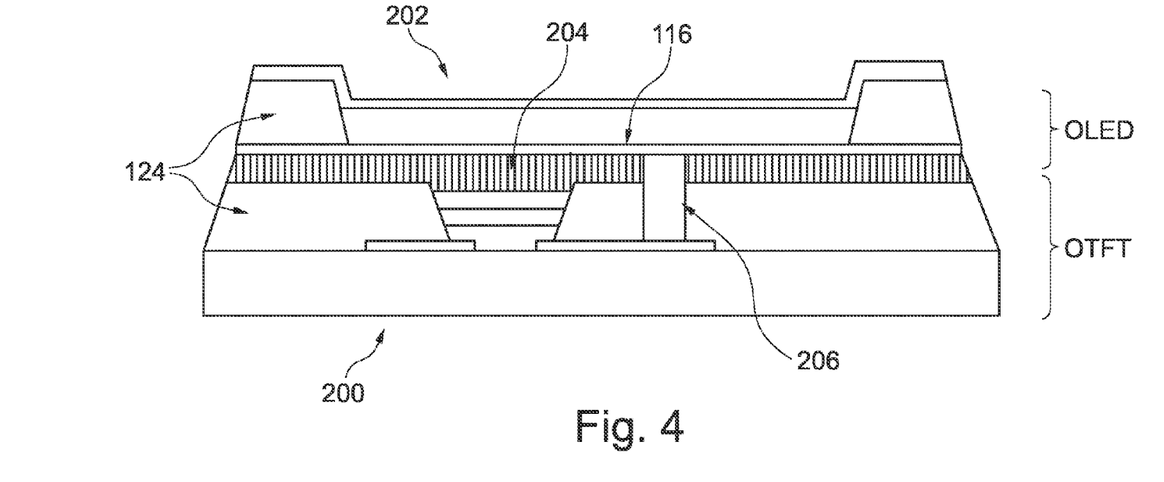

In an alternative arrangement illustrated in FIG. 4, an organic thin film transistor 200 may be fabricated in a stacked relationship to an organic light emitting device 202. In such an embodiment, the organic thin film transistor 202 is built up as described above in either a top or bottom gate configuration. As with the embodiment of FIG. 3, the active areas of the OTFT 200 and OLED 202 are defined by a patterned layer of photoresist 124, however in this stacked arrangement, there are two separate bank layers 124—one for the OLED 202 and one for the OTFT 200. A planarization layer 204 (also known as a passivation layer) is deposited over the OTFT 200. Exemplary passivation layers 204 include BCBs and parylenes. The organic light emitting device 202 is fabricated over the passivation layer 204 and the anode 116 of the organic light emitting device 202 is electrically connected to the drain electrode 112 of the OTFT 200 by a conductive via 206 passing through passivation layer 204 and bank layer 124.

Intermediate 1

To a suspension of 1,5-dichloroanthraquinone (6.8 g, 24.6 mmol) in dry toluene (100 ml) under nitrogen, was added drop wise a solution of 4-octylphenylmagnesium bromide [prepared from 4-octyl benzene (20.9 g, 74.3 mmol) and magnesium turnings (2.14 g, 89.2 mmol) in dry THF (60 ml)].

After the addition was complete, the THF was distilled off and the deep red solution stirred at reflux for 16 hrs. The mixture was diluted with AcOH:H$_2$O [150:700 ml], the toluene removed under reduced pressure and the residue extracted into ether and washed with an aqueous solution of NaOH (7.3 g) and Na$_2$SO$_4$ (60 g, in 400 ml H$_2$O). The mixture was then dried over MgSO$_4$ and concentrated in vacuum.

To a solution of the residue in AcOH (70 ml) was added HI (10 ml) and the mixture stirred at 100° C. for 30 mins. The resulting solid was isolated by filtration, washed with water (500 ml) and dried under vacuum at 50° C. It was then heated under reflux in hexane, cooled, filtered and slurried over acetonitrile to give the desired product as a yellow solid [(7.7 g, 17%) m/z 623 (M$^+$), 588 (M$^+$−Cl), 553 (M$^+$−2×Cl)], having the structure:

EXAMPLE 1

A suspension of Intermediate 1 (7.5 g, 12.0 mmol), KOH (16.1 g, 288 mmol) and quinoline (216 ml) was heated at 230° C. for 3 hrs. The resulting red solution was allowed to cool to room temperature, diluted with toluene (300 ml) and washed with water (2×150 ml), 2M HCl (2×150 ml), brine (2×150 ml), dried over MgSO$_4$ and concentrated in vacuum.

The red solid was transferred to a Soxhlet thimble (33×100 mm) and extracted with acetonitrile (600 ml). Purification of the product by sublimation (260° C. and pressure of 2×10$^{-6}$ mbar) gave the desired product as a dark red solid [(0.75 g, 11%, HPLC 99.3%), m/z 552 (M$^+$+2×H)), 550 (M$^+$), 451, 352] having the structure:

EXAMPLE 2

Organic field effect transistor devices using compound of Example 1 as the active layer were fabricated in a top gate, bottom contact device. Gold source drain contacts were defined by lift off on a glass substrate. Channel lengths of 10-200 μm and widths of 2 mm were defined. Devices were fabricated by spin-coating the compound of Example 1, onto the cleaned substrates, from a 1.5% (w/v) mesitylene solution at 1000 rpm for 30 seconds. The film subsequently dried on a hotplate at 80° C. for 10 minutes and cooled on a metal block for 1 minute.

A fluorinated dielectric material was spin-coated from a fluorosolvent on to the semiconductor layer, and dried on a hotplate at 80° C. for 10 minutes and cooled on a metal block for 1 minute. An 80 nm thick layer of aluminum as a gate electrode was thermally evaporated.

The highest mobility in saturation observed was 0.025 cm$^2$/Vs at 20 μm channel length; an on/off ratio of 4.5×10$^4$ was obtained (as measured from +20V to −40V gate bias).

A contact resistance of 97 kOhm-cm was calculated by the extrapolation method at −40V Vg or a gate-source field of −16V/100 nm dielectric.

It will be appreciated that pixel circuits comprising an OTFT and an optically active area (e.g. light emitting or light sensing area) may comprise further elements. In particular, the OLED pixel circuits of FIGS. 5 and 6 will typically comprise least one further transistor in addition to the driving transistor shown, and at least one capacitor. It will be appreciated that the organic light emitting devices described herein may be top or bottom-emitting devices. That is, the devices may emit light through either the anode or cathode side of the device. In a transparent device, both the anode and cathode are transparent. It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminum.

Transparent cathodes are particularly advantageous for active matrix devices because emission through a transparent anode in such devices may be at least partially blocked by OTFT drive circuitry located underneath the emissive pixels as can be seen from the embodiment illustrated in FIG. 4.

Thicknesses of the gate electrode, source and drain electrodes may be in the region of 5-200 nm, although typically 50 nm as measured by Atomic Force Microscopy (AFM), for example.

Other layers may be included in the device architecture. For example, in addition to providing a self assembled monolayer (SAM) on the gate, source or drain electrodes, a SAM may be provided on the substrate, insulating layer and organic semiconductor material to promote crystallinity, reduce contact resistance, repair surface characteristics and promote adhesion where required. In particular, the dielectric surface in the channel region may be provided with a monolayer comprising a binding region and an organic region to improve device performance, e.g. by improving the organic semiconductor's morphology (in particular polymer alignment and crystallinity) and covering charge traps, in particular for a high k dielectric surface. Exemplary materials for such a monolayer include chloro- or alkoxy-silanes with long alkyl chains, e.g. octadecyltrichlorosilane.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A semiconducting compound having the structure:

where n is an integer between 2 and 10,000 such that the compound is a polymer or oligomer;
where $X^1$ and $X^2$ are independently S, Se, $SiR^1R^2$, O, $CR^3R^4$, $C_2R^5R^6$, N, or $NR^7$, where $R^1$ to $R^7$ independently comprise hydrogen, straight, branched, or cyclic alkyl, akenyl, or alkynyl groups, alkoxy, aryl, silyl, or amino;
where each of $Ar^1$ to $Ar^4$ is optional and is independently, if present, an aryl or heteroaryl group;
and where $Y^1$ to $Y^4$ independently are selected from the group consisting of hydrogen, reactive or polymerizable groups, optionally substituted straight, branched, or cyclic alkyl, alkoxy, akenyl, alkynyl, amido, or amino groups, and optionally substituted aryl or heteroaryl, where at least one of $Y^1$ to $Y^4$ is not hydrogen.

2. The semiconducting compound according to claim 1, where the compound is a polymer or a copolymer.

3. The semiconducting compound according to claim 1, where n is an integer between 2 and 10.

4. The semiconducting compound according to claim 1, where $Ar^1$ to $Ar^4$ independently are heterocyclic groups having a heteroatom selected from the group consisting of S, O, Si, N, and Se.

5. The semiconducting compound according to claim 1, wherein at least one of $Y^1$ to $Y^4$ is a solubilizing group.

6. The semiconducting compound according to claim 5, wherein the solubilizing groups of $Y^1$ to $Y^4$ independently are an optionally substituted straight, branched, or cyclic alkyl, alkoxy, akenyl, alkynyl, amido, or amino groups.

7. The semiconducting compound according to claim 1, wherein $Y^1$ and $Y^3$ or $Y^2$ and $Y^4$ comprise reactive or polymerizable groups.

8. The semiconducting compound according to claim 7, wherein the reactive or polymerizable groups independently are halogens, boronic acids, diboronic acids, esters of boronic and diboronic acids, alkylene groups, or stannyl groups.

9. An electronic device comprising a semiconducting compound according to claim 1.

10. A solution for applying to the surface of a substrate to form a semiconducting portion on the substrate, the solution comprising a compound according to claim 1.

11. A method of manufacturing an electronic device comprising applying a solution according to claim 10 onto a substrate.

12. A semiconducting compound according to claim 1, wherein the compound comprises a structure selected from the group consisting of:

where TIPS is triisopropylsilyl and $F_8$ comprises the structure:

* * * * *